United States Patent
Caban et al.

(10) Patent No.: US 11,580,877 B2
(45) Date of Patent: Feb. 14, 2023

(54) MOVEMENT RECONSTRUCTION CONTROL SYSTEM

(71) Applicant: ONWARD MEDICAL N.V., Eindhoven (NL)

(72) Inventors: Miroslav Caban, Eindhoven (NL); Niek Borgers, Eindhoven (NL); Urs Keller, Eindhoven (NL); Joachim von Zitzewitz, Eindhoven (NL); Jurriaan Bakker, Eindhoven (NL); Vincent Delattre, Eindhoven (NL); Emmanuel Pignat, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 637 days.

(21) Appl. No.: 16/682,909

(22) Filed: Nov. 13, 2019

(65) Prior Publication Data
US 2020/0152078 A1 May 14, 2020

(30) Foreign Application Priority Data
Nov. 13, 2018 (EP) .................................... 18205814

(51) Int. Cl.
*G05B 13/04* (2006.01)
*G09B 19/00* (2006.01)
*G05B 13/02* (2006.01)

(52) U.S. Cl.
CPC ......... *G09B 19/003* (2013.01); *G05B 13/028* (2013.01); *G05B 13/042* (2013.01)

(58) Field of Classification Search
CPC ... G09B 19/003; G05B 13/028; G05B 13/042
See application file for complete search history.

(56) References Cited

U.S. PATENT DOCUMENTS 5,643,332 A * 7/1997 Stein .................. A61N 1/36003
607/149
7,742,037 B2 6/2010 Sako et al.
(Continued)

FOREIGN PATENT DOCUMENTS

EP 2868343 A1 5/2015
EP 2966422 A1 1/2016
(Continued)

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Gary Collins
(74) *Attorney, Agent, or Firm* — Finnegan, Henderson, Farabow, Garrett & Dunner, LLP

(57) ABSTRACT

The present invention relates to a control system for a movement reconstruction and/or restoration system for a patient, comprising a movement model generation module to generate movement model data information, an analysis module receiving and processing data provided at least by the movement model generation module, wherein the control system is configured and arranged to prepare and provide on the basis of data received by the movement model generation module and the analysis module a movement model describing the movement of a patient and providing, on the basis of the movement model, stimulation data for movement reconstruction and/or restoration.

15 Claims, 8 Drawing Sheets

(56) References Cited

U.S. PATENT DOCUMENTS

| | | | |
|---|---|---|---|
| 8,326,569 | B2 | 12/2012 | Lee et al. |
| 2006/0015470 | A1* | 1/2006 | Lauer ................. A61N 1/36003 |
| | | | 600/300 |
| 2015/0196231 | A1 | 7/2015 | Ziaie et al. |
| 2017/0156662 | A1* | 6/2017 | Goodall ............... A61B 5/7282 |
| 2019/0247650 | A1* | 8/2019 | Tran ..................... A61N 1/3704 |

FOREIGN PATENT DOCUMENTS

| | | |
|---|---|---|
| EP | 3184145 A1 | 6/2017 |
| WO | 0234331 A2 | 5/2002 |
| WO | 2010021977 A1 | 2/2010 |
| WO | 2012080964 A1 | 6/2012 |
| WO | 2017058913 A1 | 4/2017 |
| WO | 2017062508 A1 | 4/2017 |

OTHER PUBLICATIONS

Merrill, D. et al., "Electrical stimulation of excitable tissue: design of efficacious and safe protocols," Journal of Neuroscience Methods, vol. 141, No. 2, Feb. 15, 2005, 28 pages.

Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Van Den Brand, R. et al., "Restoring Voluntary Control of Locomotion after Paralyzing Spinal Cord Injury," Science, vol. 336, No. 6085, Jun. 1, 2012, 5 pages.

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," BRAIN: A Journal of Neurology, vol. 137, No. 5, May 2014, Available Online Apr. 8, 2014, 16 pages.

Danner, S. et al., "Human spinal locomotor control is based on flexibly organized burst generators," BRAIN: A Journal of Neurology, vol. 138, No. 3, Mar. 2015, Available Online Jan. 12, 2015, 12 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

* cited by examiner

| Fiber type | Diameter (μm) | Function |
|---|---|---|
| Ia (A-α) | 12-20 | Proprioception from muscle spindles |
| Ib (A-α) | 12-20 | Proprioception from Golgi tendon organs |
| II (A-β) | 5-12 | Fine touch, (2-point discrimination & vibration) |
| III (A-δ) | 2-5 | Light touch, fast pain & temperature |
| IV (C) | 0.5-1 | Slow pain & temperature |

Fig. 3

| # | FMB | Agonist | Antagonist |
|---|---|---|---|
| 1 | Right Ankle Extension | Right medial gastrocnemius, soleus | Right tibialis anterior |
| 2 | Right Ankle Flexion | Right tibialis anterior | Right medial gastrocnemius, soleus |
| 3 | Right Knee Extension | Right rectus femoris, vastus lateralis | Right iliopsoas, semitendinosus |
| 4 | Right Hip Extension | Right gluteus maximus, semitendinosus | Right iliopsoas, rectus femoris |
| 5 | Right Hip Flexion | Right iliopsoas, rectus femoris | Right gluteus maximus, semitendinosus |
| 6 | Right Trunk Stability | Right paraspinal muscles | |
| 7 | Left Ankle Extension | Left medial gastrocnemius, soleus | Left tibialis anterior |
| 8 | Left Ankle Flexion | Left tibialis anterior | Left medial gastrocnemius, soleus |
| 9 | Left Knee Extension | Left rectus femoris, vastus lateralis | Left iliopsoas, semitendinosus |
| 10 | Left Hip Extension | Left gluteus maximus, semitendinosus | Left iliopsoas, rectus femoris |
| 11 | Left Hip Flexion | Left iliopsoas, rectus femoris | Left gluteus maximus, semitendinosus |
| 12 | Left Trunk Stability | Left paraspinal muscles | |

Fig. 5

FMB/CMB used in Task 1

| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

FMB/CMB used in Task 2

| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

Fig. 6

MOVEMENT RECONSTRUCTION CONTROL SYSTEM

CROSS-REFERENCE TO RELATED APPLICATION

The present application claims priority to European Patent Application No. 18205814.9, filed on Nov. 13, 2018. The entire contents of the above-listed application is hereby incorporated by reference for all purposes.

TECHNICAL FIELD

The present invention relates to a system for controlling a movement reconstruction and/or restoration system for a patient, e.g. in the field of improving recovery after neurological disorders like spinal cord injury (SCI), for example after trauma.

BACKGROUND AND SUMMARY

Decades of research in physiology have demonstrated that the mammalian spinal cord embeds sensorimotor circuits that produce movement primitives (cf. Bizzi E. et al., *Modular organization of motor behavior in the frog's spinal cord. Trends in neurosciences* 18, 442-446 (1995); Levine A J. et al., *Identification of a cellular node for motor control pathways. Nature neuroscience* 17, 586-593 (2014)). These circuits process sensory information arising from the moving limbs and descending inputs originating from various brain regions in order to produce adaptive motor behaviors.

A spinal cord injury (SCI) interrupts the communication between the spinal cord and supraspinal centers, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R. et al., *Restoring Voluntary Control of Locomotion after Paralyzing Spinal Cord Injury. Science* 336, 1182-1185 (2012); Angeli C A. et al., *Altering spinal cord excitability enables voluntary movements after chronic complete paralysis in humans. Brain: a journal of neurology* 137, 1394-1409 (2014); Harkema S. et al., *Effect of epidural stimulation of the lumbosacral spinal cord on voluntary movement, standing, and assisted stepping after motor complete paraplegia: a case study. The Lancet* 377, 1938-1947 (2011); Danner S M et al., *Human spinal locomotor control is based on flexibly organized burst generators. Brain: a journal of neurology* 138, 577-588 (2015); Courtine G. et al., *Transformation of nonfunctional spinal circuits into functional states after the loss of brain input. Nature neuroscience* 12, 1333-1342, (2009); Capogrosso M et al., *A brain-spine interface alleviating gait deficits after spinal cord injury in primates. Nature* 539, 284-288, (2016)).

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, the system comprising means for applying to a subject neuromodulation with adjustable stimulation parameters, said means being operatively connected with a real-time monitoring component comprising sensors continuously acquiring feedback signals from said subject. The feedback signals provide features of motion of a subject, wherein the real-time monitoring component is operatively connected with a signal processing device receiving feedback signals and operating real-time automatic control algorithms. This known system improves consistency of walking in a subject with a neuromotor impairment. A Real-Time Automatic Control Algorithm is used, comprising a feedforward component employing a single input-single output model (SISO), or a multiple input-single output (MISO) model. Reference is also made to Wenger N. et al. *Closed-loop neuromodulation of spinal sensorimotor circuits controls refined locomotion after complete spinal cord injury, Science Translational Medicine*, 6, 255 (2014).

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

EP 3 184 145 A1 discloses systems for selective spatiotemporal electrical neurostimulation of the spinal cord. A signal processing device receiving signals from a subject and operating signal-processing algorithms to elaborate stimulation parameter settings is operatively connected with an Implantable Pulse Generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system advantageously allows achieving effective control of locomotor functions in a subject in need thereof by stimulating the spinal cord, in particular the dorsal roots, with spatiotemporal selectivity.

EP 2 652 676 A1 relates to a gesture control for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heartbeat, walking, etc. Similar solutions for tapping detection of a user are known from U.S. Pat. Nos. 8,326,569 and 7,742,037.

WO 2017/062508 A1 discloses a system for controlling a therapeutic device and/or environmental parameters including one or more body worn sensor devices that detect and report one or more physical, physiological, or biological parameters of a person in an environment. The sensor devices can communicate sensor data indicative of the one or more physical, physiological, or biological parameters of a person to an external hub that processes the data and communicates with the therapeutic device to provide a therapy (e.g., neuromodulation, neurostimulation, or drug delivery) as a function of the sensor data. In some embodiments, the therapeutic device can be implanted in the person. In some embodiments, the therapeutic device can be in contact with the skin of the person. The sensor devices can also communicate to the hub that communicates with one or more devices to change the environment as a function of the sensor data.

WO 2010/021977 describes an orthotic apparatus for use in providing improved range of motion which allows the amount of stretch to be hydraulically powered and measured by the device but controlled by the user. Because the apparatus accurately calculates the amount of stretch, the user, together with the user's physician and therapist, can develop a rehabilitation plan based on accurate measurements. Progress is based on tangible results rather than the user's ability to tolerate pain.

EP 2 966 422 A1 describes a method for measuring parameters, such as human weight in motion. The method provides registration of signals generated by load sensors disposed in shoe insoles. Each insole has at least two load sensors, with one mounted near the heel region and the other near the toe region of foot. The specific type of motor activity is determined based on temporal correlation of the load sensor signals from both insoles and values thereof. The person's weight, including additionally carried weight, is determined by summing up load sensor signals, for a specific type of motor activity. The invention provides for the measurement of person's weight, including additionally carried weight, in real-time for different types of motor activity, such as running, walking at different pace, standing.

WO 2017/058913 relates to systems and methods to analyze gait, balance or posture information extracted from data collected by one or more wearable and connected sensor devices with sensors embedded there within. The embedded sensors include a three-axis accelerometer, a three-axis gyroscope and an array of pressure sensors. Sensor data detected by the sensors can be received by a mobile computing device, which can analyze the sensor data to identify a pattern related to gait, balance or posture within the sensor data; and apply a statistical/machine learning-based classification to the pattern related to gait, balance or posture to assign a clinical parameter to the pattern characterizing a risk of a slip, trip and fall event.

US 2015/196231 discloses a method for acquiring gait parameters of an individual. The method includes capturing calibration images from foot marker placed on feet or shoes of an individual while an individual is standing still, the calibration images are obtained from a camera worn by the individual, capturing subsequent time-varying images from the foot markers while the individual is walking, and comparing the calibration images to the subsequent time-varying images by a processing unit that is coupled to the camera to determine changes between the initial relative image size of the foot markers and the time-varying images of the foot markers as a function of time to analyze gait of the individual.

According to the state of the art, smooth movements comparable to healthy subjects still cannot be achieved by the subject. There is a desire to have a system which overcomes the drawbacks of the prior art. In particular, there is the need of a system stimulating the patient not as a robot but to stimulate the patient's control loops within their body. A good roll of the foot and no parasite movements are necessary during walking. Thus, the goal of applying stimulation is not to control the patient as a robot, but to support the patient during training and daily life activities, e.g. walking cadence. Hence, a control system should be able to determine a movement event, e.g. a gait event with criteria that are common to all kind of healthy or pathological movement, e.g. gait, and should support the patient's own natural control loop composed of the brain, nervous system, and sensory organs.

It is an object of the present invention to improve a neurostimulation system, e.g. in the field of improving recovery after neurological disorders like spinal cord injury (SCI), for example after trauma, especially in adding a control system for a movement reconstruction and/or restoration system for a patient.

This object is solved according to the present invention by a control system for a movement reconstruction and/or restoration system for a patient, with the features of claim 1. Accordingly, a control system for a movement reconstruction and/or restoration system for a patient is provided, comprising a movement model generation module to generate movement model data information;

an analysis module receiving and processing data provided at least by the movement model generation module;

wherein the control system is configured and arranged to prepare and provide on the basis of data received by the movement model generation module and the analysis module a movement model describing the movement of a patient and providing, on the basis of the movement model, stimulation data for movement reconstruction and/or restoration.

The invention is based on the basic idea that in the context of neuromodulation, especially neurostimulation, the electrical stimulation parameters defining the stimulation in a movement reconstruction and/or restoration system for a patient can be controlled with said system, wherein a movement model is prepared and provided on the basis of model data. Such model data may be based on inter alia recent sensor data of the movement of the patient and a previous movement model, and on the basis of the movement model, stimulation of data for movement reconstruction and/or restoration is provided. Movement kinematics are calculated using rigorous mathematical protocols and movement abnormalities are identified. The control system may interfere with the feedback loop of the patient, as control inputs are identified that are required for the control system to produce the correct stimulation. Altogether, this enables motion, e.g. a gait cycle, with regular characteristics, comparable to a healthy subject.

The system can be used for treatment related but not limited to restoring and or training of the movements of the patient. Such a movement could be e.g. walking, running, stepping, swimming, rowing or cycling, or any other cyclic or non-cyclic movement.

By directly and/or indirectly attaching one or more sensors to the head and/or the neck and/or the trunk and/or the abdomen and/or the waist and/or at least one limb and/or part of a limb and/or foot motion parameters (including but not limited to position and/or angular velocity and/or angle) of the respective body parts can be determined during motion, e.g. gait cycle, to realize the reorganization of the various phases, e.g. gait phase.

Neural stimulation may be achieved by electrical stimulation, optogenetics (optical neural stimulation), chemical stimulation (implantable drug pump), ultrasound stimulation, magnetic field stimulation, mechanical stimulation, etc.

Known electrical stimulation systems use either Central Nervous System (CNS) stimulation, especially Epidural Electrical Stimulation (EES), or Peripheral Nervous System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso M et al., *A Computational Model for Epidural Electrical Stimulation of Spinal Sensorimotor Circuits, Journal of Neuroscience*, 33 (49), 19326-19340 (2013); Courtine G. et al., *Transformation of nonfunctional spinal circuits into functional states after the loss of brain input, Nat Neurosci.* 12(10), 1333-1342 (2009); Moraud E M. et al., *Mechanisms Underlying the Neuromodulation of Spinal Circuits for Correcting Gait and Balance Deficits after Spinal Cord Injury, Neuron*, 89(4), 814-828 (2016)). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low, and the imprecisions hinder fluidity and full functionality in the potential space of the movement.

PNS stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

It is possible to provide neuromodulation and/or neurostimulation with the system to the CNS and to the PNS. Both CNS and PNS can be stimulated at the same time or also intermittently or on demand. These two complementary stimulation paradigms can be combined into one strategy and made available for a patient being equipped with the system. For example, neuromodulation and/or neurostimulation of the CNS may be used to enhance and/or restore the patient's capabilities of movement, especially in a way that the existing ways of physiological signal transfer in the patient's body is supported such that the command signals for body movement or the like still are provided by the patient's nervous system and just supported and/or enhanced or translated by the CNS stimulation module. The stimulation provided by the PNS module may be used to specifically steer and direct stimulation signals to specific peripheral nervous structures in order to trigger a specific movement and/or refine existing movements. Such a PNS stimulation may be used to refine and/or complete motion and/or movement capabilities of the patient being equipped with the system. It can be e.g. used to complete flexion or extension, lifting, turning or the like of inter alia but not limited to toes, fingers, arms, feet, legs or any extremities of the patient. This can be e.g. done in cases where it is realized that the neuromodulation and/or neurostimulation provided by the CNS stimulation module is not sufficient to complete a movement or intended status of the patient. Then, such a movement or intended status may be completed or supported by stimulation provided by the PNS stimulation system. The PNS stimulation can be also used to reduce side effects or compensate for imprecisions of the CNS stimulation.

EES can be phasic or tonic, selective PNS is always phasic. Phasic is defined as locked to defined events in the sensing signals (decoded intention, continuous decoding, muscle activity onset, movement onset, event during defined movement (foot off or foot strike during gait for instance).

By PNS stimulation, a stimulation of the upper limb nerves, i.e. the radial, ulnar and/or median nerves can be provided. Also, the lower limb nerves like the sciatic and/or femoral nerves can be provided by PNS stimulation. All PNS stimulation can be done by targeting one of the above-mentioned nerves with intra-neural electrodes (transversal or longitudinal) or epi-neural (cuff) electrodes.

By CNS stimulation the following nervous structures may be stimulated: for the upper limb movements the cervical spinal cord or hand/arm motor cortex may be stimulated with the CNS stimulation module. For the lower limb movements, the lumbosacral spinal cord may be stimulated. All these nerves can be targeted with epidural, subdural or intra-spinal/intra-cortical stimulation.

Both PNS and CNS stimulation modules may be for example but not limited to implantable pulse generators (IPGs) for a neuromodulation system or the like.

IPGs can be used for providing the necessary stimulation current and signals for the CNS stimulation system and the PNS stimulation system. The IPG produces the stimulation pulses that are delivered by a lead with multiple electrodes to the stimulation side, e.g. spinal cord. For EES, the lead is positioned in the epidural space (i.e. on the outside of the dural sac, which encases the spinal cord and the cerebrospinal fluid in which the spinal cord 'floats'), on top of the spinal cord (including but not limited to the segments T12, L1, L2, L3, L4, L5, and S1 bilaterally).

It is also possible that two separated IPGs are provided, one for the PNS stimulation system and one for the CNS stimulation system.

The stimulation parameters for the PNS stimulation and the EES stimulation may be frequency, amplitude, pulse-width and the like.

Both CNS and PNS stimulations, as well as the combination of these stimulation systems may be used in a sub-motor threshold region, i.e. an amplitude or configuration at which neuronal sensation but no motor response is evoked.

The stimulation may be performed in an open-loop manner, where a pre-defined fixed stimulation is executed without adapting to e.g. the motion of the patient. The stimulation settings may then be determined by the therapist or physiotherapist. The movement of the patient is recorded.

The stimulation may be performed in a closed-loop manner, where feedback is used to adjust the stimulation to movement of the patient, including but not limited to walking or cycling.

The system may be also applied for a patient being supported by an external device, including but not limited to an exoskeleton, body-weight support, a walker, or crutches.

Said sensor input data are provided by one or more motions sensors. In particular, it is possible that two or more sensors form a sensor network.

Said sensor may comprise at least one of an inertial measurement unit (IMU), a piezo element, a velocity sensor, an accelerometer, a magnet sensor, a pressure sensor, a displacement sensor, a contact sensor, a goniometer, a magnetic field sensor, a hall sensor and/or a gyroscope and/or motion tracking video camera, or infra-red camera.

Some sensors may be worn by the patient without acquiring fixed base station, including but not limited to piezo elements, pressure sensors and/or torque sensors.

Said sensor may be configured and arranged to be inserted and/or integrated into and/or onto an exoskeleton, tights, a belt, straps, a stretching band, a knee sock, a sock and/or a shoe of the patient.

Said sensor may be intended to be placed on the foot to get to most information possible about the movement, e.g. gait.

In particular, two or more sensors placed on one foot and/or any other suitable position of the body such as another part of a leg, including but not limited to the shank and/or thigh and/or hip and/or other parts of the body including but not limited to the trunk and/or the abdomen and/or one or two arms and/or one or two hands and/or another part of an arm and/or the head and/or the neck of the patient may provide a precise description of the cadence, swing, stance, heel strike, heel lift and toe-off can be identified. The same events and parameters can be identified for the other foot and/or another part of a leg, including but not limited to the shank and/or thigh and/or hip and/or other parts of the body including but not limited to the trunk and/or the abdomen and/or one or two arms and/or one or two hands and/or another part of the arm and/or the head and/or the neck of the patient. By combining signals of the sensors, together with the movement, e.g. gait phase and cadence of the stimulation input, a reliable movement phase, e.g. gait phase and cadence estimate can be provided.

Said sensors may be lightweight and wearable, thus the sensors may not hamper the movement of the patient.

In particular, said sensor may be placed at different positions in the shoe or into the shoe sole and/or into the shoe insole. One shoe and/or one shoe sole and/or one shoe insole may be equipped with one or more sensors. Said sensors may be placed in the heel area and/or the metatarsal area and/or the toe area.

Said IMU may measure and report 3D accelerations, 3D angular velocities and 3D orientation using a combination of one or more of an accelerometer, one or more of gyroscopes, and optionally one or more of a magnetometer. Optionally, a temperature sensor may also be included to compensate for the effect of temperature on sensor readings. By integrating the angular velocity assessed by said one or more gyroscopes and fusing with data from said one or more accelerometers, it may be possible to get a precise measurement of the angle of the foot and/or another part of a leg, including but not limited to the shank and/or thigh and/or hip and/or other parts of the body including but not limited to the trunk, and/or one or two arms and/or one or two hands and/or another part of an arm and/or the head and/or the neck of the patient. This angle may have a regular and characteristic pattern for a healthy subject but not for an injured patient. Based on these measurements the orientation of the IMU with respect to the fixed world can be estimated accurately, using standard sensor fusion algorithms.

Body part position such as foot position, shank position, trunk position, arm position, thigh position, ankle position, shoulder position, head position or the like estimates can be obtained by double integration of the measured acceleration in combination with drift correction. In this way, non-real-time reconstruction of e.g. foot trajectories (or any other trajectories of a body part) can be done up to a few centimeters accuracy for healthy subjects. Any such body position alone or in combination with other positions and especially the change of such positions can be used to describe and calculate a movement or movement phase.

The control system may comprise a preprocessing module for preprocessing the sensor input data The preprocessing module may preprocess the sensor data. In particular, the preprocessing of data may be based on algorithms that use a series of measurements observed over time, containing statistical noise and other inaccuracies, and produce estimates of unknown variables that tend to be more accurate than those based on a single measurement, by estimating a joint probability distribution over the variables for each timeframe.

The preprocessing module may be configured and arranged to and/or responsible for shifting, compressing, and normalizing the raw data into a format that improves the performance of the subsequent modules In particular, such a preprocessing module may be or comprise a Kalman filter or any other suitable filter.

Preprocessing may be used especially in connection with machine learning or self-learning systems and/or algorithms.

In general, learning algorithms benefit from standardization of the data set. If some outliers are present in the set, robust scalers or transformers are more appropriate.

Standardization of datasets is a common requirement for many machine learning estimators in machine learning systems and algorithms; they might behave badly if the individual features do not more or less look like standard normally distributed data, e.g. Gaussian with zero mean and unit variance. In practice the shape of the distribution is often ignored and just transformed the data to center it by removing the mean value of each feature, then scale it by dividing non-constant features by their standard deviation. For instance, many elements used in the objective function of a learning algorithm (such as the RBF kernel of Support Vector Machines or the l1 and l2 regularizers (Lasso Regression or Ridge Regression) of linear models) assume that all features are centered around zero and have variance in the same order. If a feature has a variance that is orders of magnitude larger than others, it might dominate the objective function and make the estimator unable to learn from other features correctly as expected.

In particular, by integrating the angular velocity and fusing with data from an accelerometer and preprocessing these data with a Kalman filter, it may be possible to get a precise measurement of the angle of the foot and/or another part of a leg, including but not limited to the shank and/or thigh and/or hip and/or other parts of the body including but not limited to the trunk, and/or one or two arms and/or one or two hands and/or another part of an arm and/or the head and/or the neck of the patient. This angle also has a regular and characteristic pattern for a healthy subject but not for an injured patient.

The movement model generation module may generate a movement model. The movement model generation module uses preprocessed sensor data to prepare a movement model.

The analysis module may receive, and process data provided by the preprocessing module and the movement model generation module.

In particular, the analysis module may be a real-time analysis module.

After the preprocessing step, the current state of the movement may be used to estimate the probability density function of the movement phase. The gait speed of the movement phase is retrieved a single normal distribution to be used in the filter.

The control system may further comprise an input module for receiving sensor input data, the sensor input data describing a phase of a movement.

The input module may be embodied as or comprise a Bluetooth module, which is e.g. placed on the motion controller that receives and forwards the data.

Furthermore, there may be a filter to filter the data provided by the real-time analysis module.

For example, the use of a general concept including an input module, a preprocessing module, a movement model generation module, a real-time analysis module, and a filter and made available for a movement reconstruction system for a patient being equipped with the movement reconstruction and/or restoration system enables to allow triggering neurostimulation based on sensor input data from the patient and a preexisting movement model.

In particular, the movement model generation module may be configured and arranged to prepare and provide the movement model, wherein the movement model generation module is a learning system.

At the beginning of a rehabilitation session, the movement model used may be a general model. The movement model used at the beginning of a rehabilitation session may be trained on a set of different subjects, e.g. one or more trainers, and/or one or more healthy subjects and/or one or more patients. The movement model thus may not be perfect for the individual patient but sufficient, e.g. in the case of a gait model sufficient to make some steps. Thus, the movement model may be trained by an online learning system to adapt to the patient's individual movement kinematics.

For the online learning system, it may be possible to tune the learning rate, namely, the rate at which the model adapts to change in the movement, e.g. gait cycle.

It may be possible to stop the learning process when the movement model is good enough and to store it for further sessions with the same patient.

Moreover, the control system may be configured and arranged to prepare and provide the movement model on the basis of a fusion of sensor input data and movement model.

In particular, recent sensor data from the one or more sensors may be fused to the existing movement model to update the movement model. As soon as a whole movement, e.g. a gait cycle of the patient is detected, the online learning system may determine the past movement event and the existing movement model may be trained to adapt to the new data. The movement model used online may be updated. As a result, each recently generated movement model is based on more data than the previous movement model.

Based on the movement model, the stimulation of the patient may be provided via one or more IPGs.

Moreover, the control system may comprise at least one sensor data buffer.

In particular, sensor data from one or more sensors and/or one or more sensor networks may be recorded for at least one complete movement or movement cycle, e.g. gait cycle, and stored in a sensor buffer. In particular, the sensor buffer may accumulate sensor data from one or more sensors and/or one or more sensor networks.

Furthermore, the control system may comprise at least one offline expert system.

In particular, the offline expert system may process recorded sensor data for a period of time of minimum one complete movement, e.g. gait cycle, offline. The gait phase consequently may be corresponding to the recorded data buffer. In particular, the gait phase may be created so that it may take always the same value at the same event.

In particular, offline analysis may enable to use criteria that could not be used on real-time.

We define real-time as an end-to-end latency that is less than 100 ms, preferably less than 50 ms.

Moreover, the control system may comprise at least one movement event library.

Based on the sensor data for the recorded period of time the offline expert system determines a movement event library offline and creates a movement model, e.g. gait model, for the recorded movement, e.g. gait events.

Hence, the stimulation may be at any given "time" of a movement cycle, e.g. gait cycle.

In particular, the movement event library may comprise stimulation settings for one complete movement cycle, including but not limited to a gait cycle.

In particular, for one gait cycle, the movement event library at least includes the stimulation settings for the two events foot-strike and foot-off, but also more events may be set.

Said events of the movement event library may be present amongst all kind of patient.

Furthermore, the control system may comprise at least one model training module.

In particular, the model training module integrates recorded sensor data and corresponding movement phase, e.g. gait phase. Said module may train the movement model, e.g. gait model, using recent data to adapt to the particular movement, e.g. gait of the patient using a non-linear regression technique.

In particular, the filter may be at least one of a Kalman filter, a histogram filter, a particle filter, a stochastic filter or the like.

By means of a filtering process, it may be possible to take into account estimation of previous time steps to get a movement phase that is consistent in time.

The general idea behind filtering is to establish a best estimate for the true value of the movement model from an incomplete, potentially noisy set of observations on that movement model and corresponding movement.

The Kalman filter is the estimation part of the optimal control solution to the linear-quadratic-Gaussian control problem. It is an algorithm that uses a series of measurements observed over time, containing statistical noise and other inaccuracies, and produces estimates of unknown variables that tend to be more accurate than those based on a single measurement alone, by estimating a joint probability distribution over the variables for each timeframe.

The main idea behind a Histogram filter is to run through the signal entry by entry, replacing each entry with the median of neighboring entries.

Particle filters are methods of genetic, Monte Carlo algorithms used to solve filtering problems arising in signal processing and Bayesian statistical inference. The filtering problem consists of estimating the internal states in dynamical systems when partial observations are made, and random perturbations are present in the sensors as well as in the dynamical system.

Moreover, the control system may be configured and arranged to extract at least one base frequency out of sensor input data, especially wherein the base frequency is indicative of a cadence of the movement.

Each movement, e.g. gait, may vary between two or more patients, as well as for a single patient for e.g. different walking speeds and different assistive devices, including but not limited to body-weight support, walker, crutches. Especially for impaired gait, not all gait events are always present. However, as e.g. walking is a periodic motion, all measured signals are also periodic. Hence, it is always possible to estimate the cadence by extracting the base frequency of the measured signals.

The cadence of the left foot should be equal to the cadence of the right foot and the cadence of the provided stimulation, and the left foot and right foot should be (roughly) in anti-phase. Machine-learning methods may be used to adapt the gait phase estimation to the gait of the patient. The level of agreements and discrepancies between motion of the left and right foot, and the stimulation input, may be used to give an indication of the gait phase estimation reliability. This can also be transferred to other movements, including but not limited to stepping, walking, running, swimming, cycling, rowing.

Furthermore, the control system may comprise a pre-warning module, which is configured and arranged to provide a pre-warning signal indicative of providing an upcoming stimulation event.

Regulating gait to a predefined reference interferes with voluntary motion of the patient. In particular, voluntary motion of the patient may have a large effect on the movement, as the patients voluntary control may modulate muscle activation. The movement pattern may therefore differ from comparable to a healthy subject, to impaired or reduced despite identical stimulation. The pre-warning signal may help the patient to adjust voluntary control to the respective movement planed, thus a regular movement may be performed. The pre-warning signal may include but is not limited to a sound signal, vibration, light signal, smell, taste, pain, temperature (warm, cold), humid signal, draught or the like.

In particular, the pre-warning signal may act in a sub-motor threshold region at which a sensation is evoked, but not a motor response.

In the following it is identified which control output parameters exist and their effects on the afferent nerves, as well as their end effects on muscle activation is described. Based on this, we select which output parameters will be controlled by the control system.

BRIEF DESCRIPTION OF THE FIGURES

Further details and advantages of the present invention shall now be disclosed in connection with the drawings.

It is shown in

FIG. 3 a table specifying the fiber types, diameter, and function;

FIG. 5 a table specifying the intended movement and the involved agonist muscle and the involved antagonist muscle;

FIG. 6 functional muscle blocks (FMB) and custom muscle blocks (CMB);

DETAILED DESCRIPTION

Note that in the following we primarily refer to CNS/EES stimulation. The one skilled in the art may transfer the stimulation parameters to PNS/FES stimulation.

Figure 1:
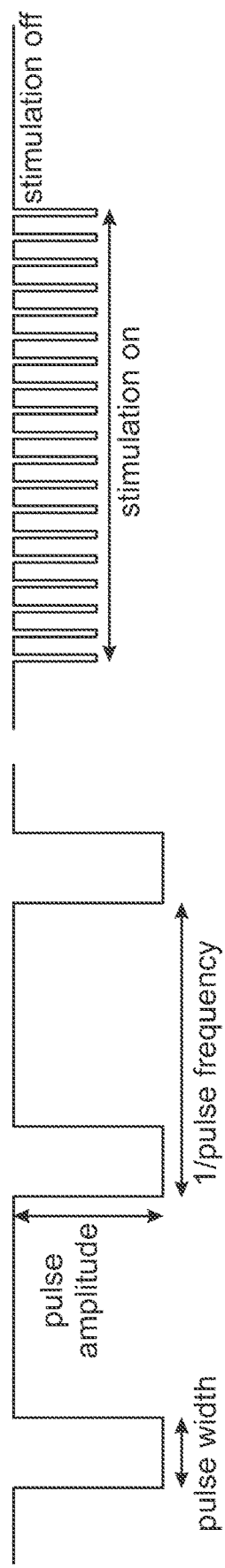
FIG. 1 a schematic, very simplified representation of a stimulation pulse delivered by a system according to the present invention.

The control system may provide stimulation data for movement reconstruction and/or restoration for stimulation of afferent nerve fibers using electrical current pulses. Given this starting point, the following stimulation parameters may be identified:

Electrode configuration (which electrodes to use, polarity)
Stimulation (Pulse) amplitude
Stimulation (Pulse) width
Stimulation (Pulse) frequency FIG. 1 illustrates a schematic, very simplified representation of the stimulation pulse, which illustrates the pulse amplitude, pulse width, and pulse frequency. Each stimulation pulse is followed by a neutralization pulse or a neutralization period (not depicted) to remove the electric charge from the tissue in order to avoid tissue damage.

The effects of each of the stimulation parameters are described below.

Electrode configuration: Stimulating a specific muscle group requires applying a specific electrical field at a specific location on the spinal cord. Therefore, the electrical stimulation may be delivered to the spinal cord by a lead with multiple electrodes. The location, shape, and direction of the electrical field that is produced may be changed by choosing a different electrode configuration (which electrodes are used, with which polarity and potential) that is used to deliver the current. Hence, the electrode configuration may determine to which spinal roots the stimulation is delivered, and therefore which subsequent muscles or muscle groups activity will be reinforced.

Figure 2A:
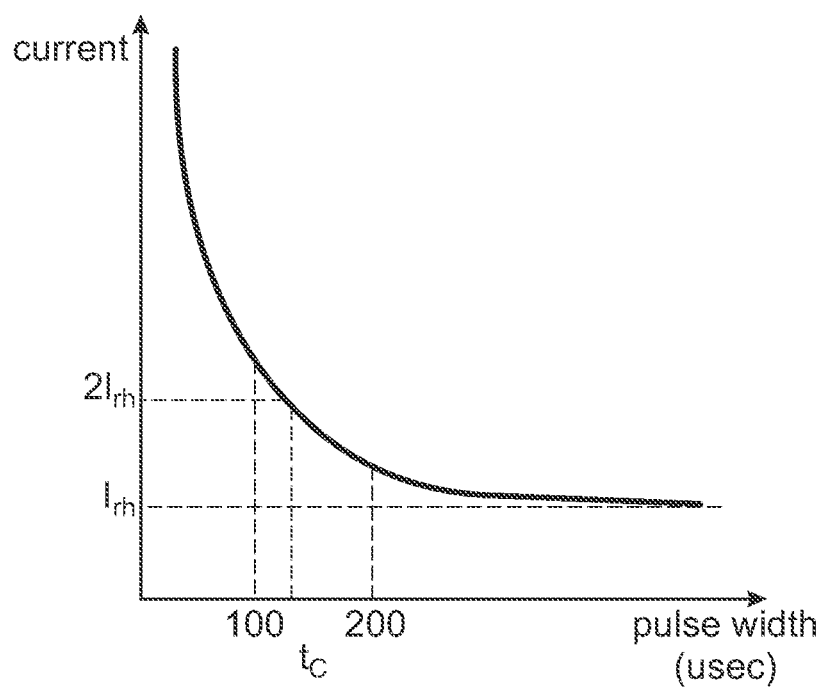
FIG. 2A, B the necessary current and necessary charge to trigger an action potential in a nerve fiber as a function of the pulse width (using a square pulse)
Figure 2B:
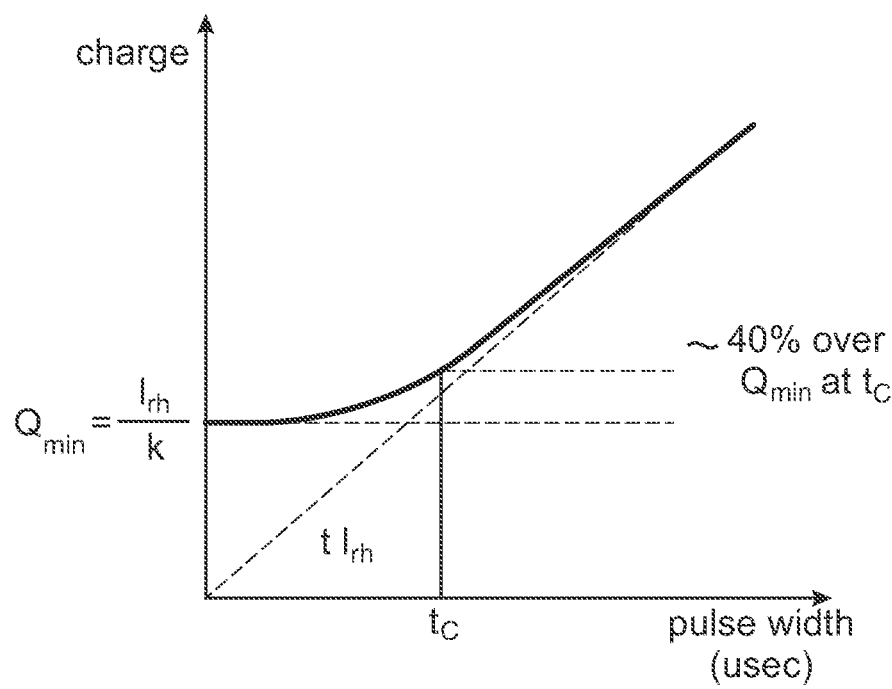

Pulse amplitude and pulse width: In FIG. 2A and FIG. 2B the necessary current and necessary charge to trigger an action potential in a nerve fiber are shown as a function of the pulse width (using a square pulse) (cf. Merrill D R. et al., *Electrical Stimulation of excitable tissue: design of efficacious and safe protocols*, J Neurosci methods 141(2):171-98 (2005)). FIG. 2A and FIG. 2B also show the rheobase current $I_{rh}$, which is the current that is required when using infinitely long pulse widths, and the chronaxie time $t_c$, which is the required pulse width at a current of $2I_{rh}$.

Although larger currents may be required at smaller pulse widths, the total required charge may decrease with decreasing pulse width, see FIG. 2B. Hence shorter pulses with higher current amplitudes may be energetically beneficial.

For smaller diameter nerves, the current-pulse width curve of FIG. 2A shifts, as smaller diameter fibers may require higher currents. Hence, a higher current may activate more nerve fibers, as also smaller diameter nerve fibers may be activated (until saturation). However, also cross-talk is increased as also more neurons from neighboring roots may be activated. Fortunately, the afferent fibers involved in motor control (fiber types Ia and Ib) may be all relatively large (12-20 µm), while the fibers involved in touch, temperature, and pain feedback (which should not be triggered) may be relatively small (0.5-12 µm), as depicted in FIG. 3. Hence, with increasing pulse width and/or current amplitude, the type Ia and Ib fibers may be the first to be recruited. This may enable recruiting (most of) the relevant fibers while keeping cross-talk and patient discomfort to a minimum.

Pulse frequency: The pulse frequency may determine the frequency of the action potentials generated in the afferent nerves, assuming sufficient charge is delivered each pulse to trigger the action potentials. As no new action potential can occur in a nerve during the refractory period, the frequency of the triggered action potentials will saturate at high pulse frequencies. This saturation point is generally at around 200 Hz for afferent fibers (Miller J P. et al., *Parameters of Spinal Cord Stimulation and Their Role in Electrical Charge Delivery: A Review. Neuromodulation: Technology at the Neural Interface* 19, 373-384, (2016)). However, stimulation at frequencies above the saturation point may still be beneficial, as by increasing frequency the total charge delivered per unit time (i.e. charge per second) can be increased without changing current amplitude or pulse width (Miller J P. et al., *Parameters of Spinal Cord Stimulation and Their Role in Electrical Charge Delivery: A Review. Neuromodulation: Technology at the Neural Interface* 19, 373-384, (2016)).

Pulse positioning: Many tasks, including walking, require simultaneous activation of multiple muscle groups. Hence, to support these tasks, multiple muscle groups may need to be stimulated simultaneously, each requiring a specific electrical field and pulse frequency. When applied simultaneously, these different electrical fields may interact with each other, potentially leading to unintended and uncontrolled effects. Therefore, to avoid this situation, care should be taken that according to the stimulation data, individual stimulation pulses and their neutralization periods targeting different muscle groups are not applied simultaneously. This may not be considered a stimulation parameter but does identify a required system feature: a pulse positioning algorithm (PPA).

The previous section describes the effect of the stimulation parameters on triggering action potentials in afferent nerve fibers. Although triggering these action potentials is an essential step in the therapy, in the end the stimulation according to the stimulation data should enable or support the patient in performing specific lower body motions, which may require the activation of specific muscles or muscle groups. The effect of the triggered action potentials in afferent nerve fibers on muscle activation may be filtered inside the spinal cord through spinal reflex circuits and modulated through the voluntary control of the patient. Hence, the effect of the stimulation parameters on muscle activation may be not perfectly clear and may be affected by intra- and inter-patient variations. The following aspects may be of relevance here:

Different patients may have different levels of voluntary control over their lower body, depending on the type and severity of their SCI lesion level and state of (spontaneous) recovery.

Stimulation of afferent nerve fibers may assist or enable activation of the corresponding muscles but may not necessarily enforce motion. The patient may modulate the activation (e.g. make a large or small step without changing the stimulation), or even resist motion of the leg completely. This may vary per patient and may change with increasing recovery.

Conjecture: Because the spinal cord floats in the cerebrospinal fluid, the distance between the spinal cord and the lead electrodes may vary (mostly as a function of the Patient's posture: prone—large distance, supine—small distance). Another hypothesis may be that due to posture changes, the layer thickness of low conductive epidural fat between the lead electrodes and the dura/cerebrospinal fluid a changing, leading to an impedance change as seen by the electrodes, and resulting in an altered current/voltage delivered stimulation by the electronics. As a result, the effect of the applied stimulation (including muscle onset and saturation) may also vary with the patient's posture. Although this conjecture is not proven, patients may successfully make use of the described effects to modulate the stimulation intensity by varying their posture: bending forward reduces the intensity, bending backward increases it.

Pulse frequencies between 40 and 120 Hz may mostly being used, although it may theoretically be possible to stimulate up to 500 Hz as this may have benefits for selectivity in muscle activation and improved voluntary control of the patient.

It may be possible that general increasing the pulse amplitude may not lead to increased recruitment of muscle fibers (with corresponding increased cross-talk), and that increasing the stimulation frequency may lead to increased muscle activation without affecting cross-talk. However, increasing the stimulation frequency may reduce the intensity of natural proprioception and result in a decreased feeling in the leg of the patient. This is probably due to the collision of natural sensory inputs with antidromic action potentials generated by the electrical stimulation. At high frequency (above 100 Hz), patients may even report a complete loss of sensation of the leg and "feel like walking with their legs being absent". This is a non-comfortable situation requiring the patient to make a leap of faith at each single step, believing that the leg that he/she does not feel anymore will support him/her during the next stance phase. Adjusting the balance between stimulation amplitude and frequency may therefore be necessary to find the optimal compromise between cross-talk limitation and loss of sensation. Simulations suggest that a possible workaround may be to shift the stimulation domain to lower amplitudes and even higher frequency, such that with a minimal number of stimulated fibers the same amount of activity is triggered in the spinal cord. Such hypothesis requires validation via additional clinical data. Finally, it may also be identified that different patients require different stimulation, i.e. that the optimal frequency and amplitude settings may vary highly between patients. Hence, the relation between stimulation amplitude and frequency on muscle activation may be still for a large part unclear. Moreover, the optimal stimulation settings may vary during the day, the assistive device that is used (crutches, walker, etc.), over time with improved recovery, and with the goal of the training or activity.

Timing: apart from applying the correct electrical field at the right location on the spinal cord, they also may need to be applied at the correct moments in time and correctly sequenced. The relevant timing aspects that are identified are listed below.

Figure 4:
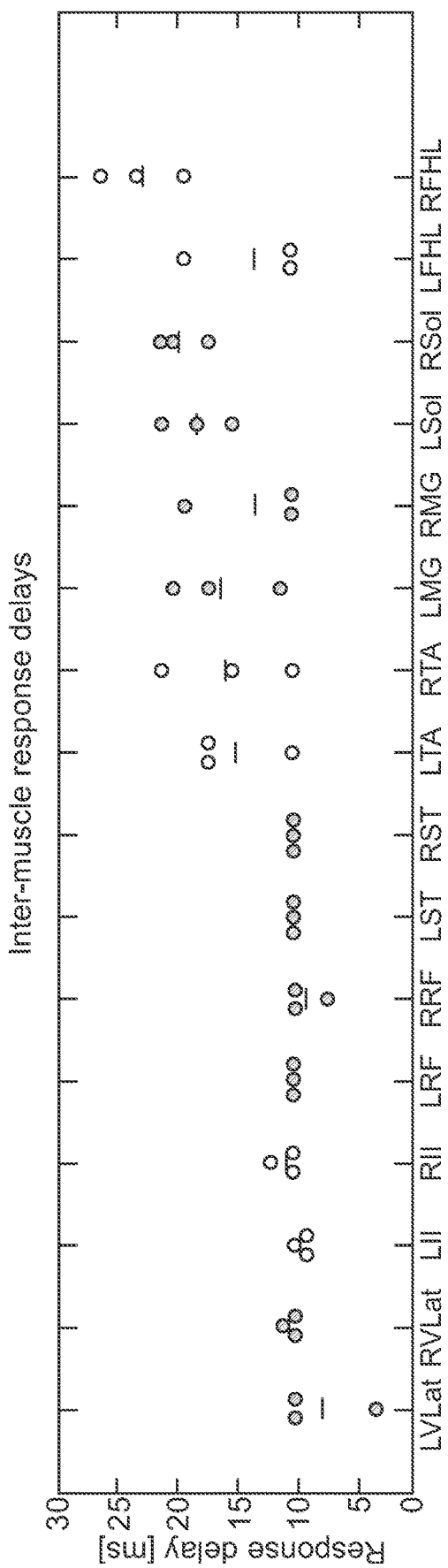
FIG. 4 the relationship between response delay and inter-muscle response delays.

There is a delay from stimulation on the spinal cord to muscle activation (typical values in the order of 0-30 ms depending on the muscle, see FIG. 4, LVLat=left vastus lateralis, RVLat=right vastus lateralis, Lll=left iliopsoas, Rll=right iliopsoas, LRF=left rectus femoris, RRF=right rectus femoris, LST=left semitendinosus, RST=right semidentinosus, LTA=left tibialis anterior, RTA=right tibialis anterior, LMG=left medial gastrocnemius, RMG=right medial gastrocnemius, LSol=left soleus, RSol=right soleus, LFHL=left flexor halluces longus, RFHL=right flexor halluces longus).

While EES enables patients to perform motions, the patient may need to be able to predict when the stimulation will occur in order to make the best use of the stimulation. Likewise, suppressing motion while stimulation is provided also requires that the patient knows when to expect the stimulation. Hence, predictability of the stimulation timing is essential.

When the stimulation is not synchronized to the patient's (intended) motion, the patient may not be able to perform a proper movement. Here, this may mean that the stimulation needs to be predictable by the patient, as the patient needs to synchronize to the stimulation.

The duration of the stimulation for leg swing during walking may need to be finely tuned. For some patients, increasing the duration of this stimulation by 100 ms made the patient jump instead of performing a proper step.

20 ms may be a sufficient resolution for tuning the stimulation timings (i.e. the on/off times of the stimulation for a specific muscle group may not need to be controlled at a precision below 20 ms). Given current data availability, controlling the timings at resolutions below 20 ms may not seem to improve the effectiveness of the stimulation.

Based on the previous sections, the stimulation parameters may be selected. This may determine the control output space that is used, and therefore the complexity of the control problem and the potential effectiveness of the control system.

First it is discussed which parameter spaces can be reduced or eliminated. The remaining control output space is summarized below.

Electrode configuration: Walking, as well as other movements of the lower extremities, may be composed of well-coordinated flexion and extension of lower body joints by contraction of agonist muscles and relaxation of antagonist muscles. The specific set of agonist and antagonist muscles for joint specific flexion and extension may be grouped, and as the number of joints is limited, this means that only a small discrete set of muscle groups may be needed to be stimulated. For each joint flexion and extension, the optimal electrode configuration will be created for activation of the agonist muscles while avoiding activation of the antagonist muscles (as well as avoiding activation of muscles on the contralateral side). This may be done in a procedure called the functional mapping. We define the Functional Muscle Blocks (FMB), as the resulting stimulation configurations for each specific muscle group. At least 12 specific FMBs have been identified for using the control system, these are listed in FIG. 5 with their corresponding agonists and antagonists.

As knee flexion and hip extension both involve the semitendinosus, it is physically not possible to target knee flexion and hip extension separately. Therefore, FIG. 5 does not include knee flexion (this could be considered redundant to hip extension).

Next to the 12 FMB listed in FIG. 5, it is also envisioned that the trainer/therapist/physiotherapist may create Custom Muscle Blocks (CMB). Creating CMB may be useful in case the trainer/therapist/physiotherapist wants to apply stimulation that does not specifically target any of the 12 muscle groups targeted by the FMB, or in case the trainer/therapist/physiotherapist wants to use a variant of one of the 12 FMB in a specific Task.

Hence, by limiting the electrode configurations to the discrete set of FMB and CMB (versus an infinite number of possible electrode configurations), the control problem complexity may be reduced considerably without significantly affecting the potential effectiveness of the control system. Stimulation for a Task is then reduced to stimulation of (a subset of) the predefined FMB and CMB, see FIG. 6. In this example, the Right Trunk Stability is used in both Task 1 and Task 2.

The functional mapping procedure may require measuring the response of each of the muscles listed in FIG. 5 with EMG sensors. Due to the large number of muscles, this requires attaching many EMG sensors to the patient (which is time consuming) and processing a large amount of data. Moreover, as motion of the patient may induce signal artifacts, the functional mapping may be best performed while the patient is not moving. For these reasons, the functional mapping procedure may be performed in a separate session using a Space Time Programmer (STP) for e.g. programming space and time of the stimulation, and not e.g. adaptively within the control system. Hence, the configuration of FMB and CMB may be considered as a given to the control system.

Pulse width: From the viewpoint of triggering action potentials in afferent nerve fibers, the parameters pulse width and pulse amplitude may be tightly linked and may together determine which afferent nerve fibers are recruited. Increasing the pulse width may allow to reduce the amplitudes and decreasing the pulse width may allow reducing energy consumption (as the total required charge for triggering an action potential decreases with decreasing pulse width, see FIG. 2B and stimulating more FMB simultaneously or at higher frequencies. However, from a control perspective the two parameters may be (almost) redundant, as increasing either parameter may lead to the recruitment of more afferent nerve fibers over a larger area.

Pulse widths below chronaxie time $t_c$ may quickly require high currents (and thus high voltages), which is difficult to produce and may lead to patient discomfort. Beyond $t_c$, the strength-duration curve of FIG. 2A is almost flat, so increasing pulse width beyond $t_c$ has little effect on the required amplitudes while it increases total power consumption. Also considering that having a fixed pulse width simplifies the pulse positioning, the pulse width is chosen to be fixed (at a value near chronaxie time $t_c$ such that both energy consumption and required current amplitudes remain low, where $t_c \approx 200$ μs for afferent dorsal root nerve fibers in humans). This reduces the complexity of the control problem by reducing the number of output parameters.

This may leave the following stimulation parameters to be controlled over time by the control system:
Which FMBs to stimulate
Stimulation amplitude per FMB
Stimulation frequency per FMB The pulse positioning may be considered a lower level problem and may therefore be not a direct output of the control system (system feature). The pulse positioning will be performed by the IPG.

Although combining amplitude and frequency to a single 'intensity' parameter has been considered, doing so is not envisioned for the control system, as these parameters may have very different effects. On triggering action potentials in afferent nerve fibers, the amplitude and frequency may be independent parameters: the amplitude determines in which afferent nerve fibers action potentials are triggered, the frequency determines the rate at which they are triggered. Hence, in principle the amplitude determines which muscle fibers are activated, the frequency determines how hard, although it is unclear if the independence of the two parameters also holds for muscle activation due to the signal processing that occurs in the spinal cord. Moreover, it may be apparent that for some patients changing the amplitude gives the best results, while for other patients the frequency may be the more useful parameter.

As the precise relation between frequency and amplitude is not known in the clinical context it may not be recommended to combine frequency and amplitude to single parameter. Hence, the stimulation frequency and amplitude may be controlled independently from each other.

In the following the principle of the sensor and the stimulation system (e.g. IPG) of the present invention are described in greater detail.

Sensors: Battery powered, body worn sensors (directly or indirectly), collecting motion data, and sending it to the controller. Its intended use is to capture body motion parameters.

Stimulation system, here IPG: Implantable Pulse Generator. A battery powered device that generates the electrical stimulation, subcutaneously implanted. Its intended use is to deliver electrical stimulation to the lead based on command received from the motion controller.

The control system may further comprise or may be linked to a programmer.

Programmer: The programmer, or also called the clinician programmer, can be used to receive inter alia stimulation parameter, patient data, physiological data, training data etc.

It may comprise a Space Time Programmer (STP) for e.g. programming space and time of the stimulation, a Physiotherapist Programmer (PTP) for e.g. allowing the physiotherapist adjustment to the stimulation, and a Patient Programmer (PP) for e.g. allowing the patient to select a specific stimulation program.

The STP, Physiotherapist Programmer (PTP), and Patient Programmer (PP) can be embodied as applications installed on a mobile device that communicate with the control system. They are used by the treating physician (TP), a physiotherapist (PT), or the patient to provide inputs to the control system, e.g., selecting, starting, and stopping a task or configuring stimulation parameters.

The programmer may allow adjusting the stimulation parameters of a task, while the task is running. This enables the user to tune the stimulation without having to start and stop the task, which would be very cumbersome at the start of the rehabilitation training, when all stimulation partitures are developed and tuned.

Generally speaking, the programmer may have the following structure:

In a first embodiment, the programmer can be embodied such that it is possible to receive inter alia but not limited to stimulation parameters, patient data and the like, check and/or reprogram the stimulation data and send it back to e.g. the control system.

The programmer is in this first embodiment capable to receive data from the implanted (part of the) system (e.g. the motion controller), display data, receive input from the user and then send it back to the control system. In other words: The programmer can receive, process and re-send the data.

In a second embodiment, the programmer may receive data from a remote database. The database may be e.g. linked with the stimulation system via a separate interface, which is configured for data transfer from the system to the database only.

The programmer is in this second embodiment capable to receive data from the remote database, display data, receive input from the user and then send it to the motion controller. In other words: The programmer is only in connection with the control system for sending data, it does not receive data from the control system or any implanted system parts.

Figure 7:
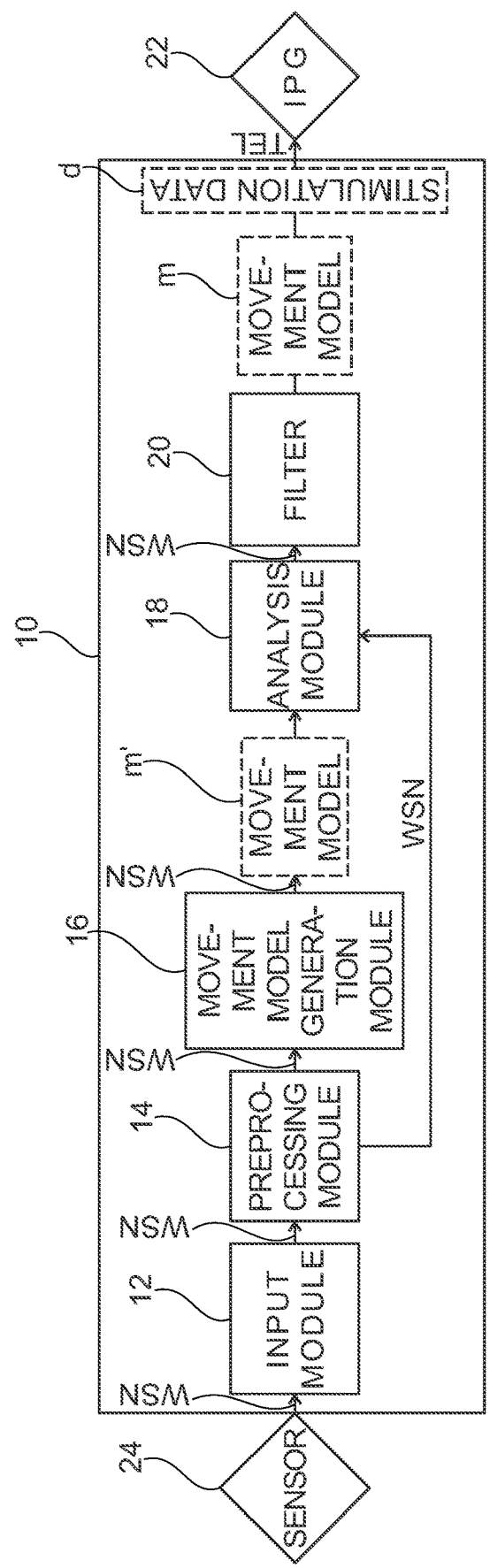
FIG. 7 a general layout of a control system for a movement reconstruction and/or restoration system for a patient according to the present invention.

FIG. 7 shows a general layout of a control system for a movement reconstruction and/or restoration system for a patient according to the present invention.

The present embodiment comprises a control system 10 for a gait reconstruction system for a patient according to the present invention.

The control system 10 comprises an input module 12.

The control system 10 also comprises a preprocessing module 14.

In this embodiment, the preprocessing module 14 is a Kalman filter.

However, also other preprocessing modules 14 are generally possible.

Furthermore, the control system 10 comprises in the shown embodiment a movement model generation module 16.

Additionally, the control system 10 comprises an analysis module 18.

In this embodiment, the analysis model 18 is a real-time analysis module 18.

The control system 10 comprises also a filter 20.

In an alternative embodiment, the control system 10 comprises more than one filter 20.

The filter 20 in the present embodiment is a particle filter 20.

However, the filter 20 could generally also be a Kalman filter, a histogram filter, a stochastic filter or the like.

The control system 10 is connected to a sensor 24 and an implantable pulse generator (IPG) 22.

The input module 12 is connected to the preprocessing module 14.

The preprocessing module 14 is connected to the movement model generation module 16.

Further, the preprocessing module 14 is connected to the real-time analysis module 18.

The movement model generation module 16 is connected to the real-time analysis module 18.

The real-time analysis module 18 is connected to the filter 20.

The connection between the input module 12 and the preprocessing module 14, the preprocessing module 14 and the movement model generation module 16, the preprocessing module 14 and the real-time analysis module 18, the movement model generation module 16 and the real-time analysis module 18, and the real-time analysis module 18 and the filter 20 is in the shown embodiment is a direct connection.

However, also an indirect connection (i.e. with another component of the control system 10 in between) would be generally possible.

The connection between the input module 12 and the preprocessing module 14, the preprocessing module 14 and the movement model generation module 16, the preprocessing module 14 and the real-time analysis module 18, the movement model generation module 16 and the real-time analysis module 18, and the real-time analysis module 18 and the filter 20 is established in the shown embodiment via a wireless network WSN.

However, also a cable-bound connection would be generally possible.

The control system 10 is connected to the sensor 24 via a wireless network WSN.

However, also a cable-bound connection would be generally possible.

The control system 10 is connected to the IPG 22 via a wireless connection TEL.

However, also a cable-bound connection would be generally possible.

The input module 12 receives sensor input data from one or more sensors 24 or one or more sensor networks directly or indirectly attached to a patient.

The input module 12 receives sensor input data, the sensor input data describing a phase of a movement.

The sensor data are transferred from the input module 12 to the preprocessing module 14 and there preprocessed.

In other words, the preprocessing module 14 preprocesses the sensor input data received from the input module 12.

In this embodiment, the preprocessing module 14 is a Kalman filter.

The Kalman filter is the estimation part of the optimal control solution to the linear-quadratic-Gaussian control problem.

The Kalman filter is an algorithm that uses a series of measurements observed over time, containing statistical noise and other inaccuracies, and produces estimates of unknown variables that tend to be more accurate than those based on a single measurement alone, by estimating a joint probability distribution over the variables for each timeframe.

However, also other embodiments of a preprocessing module 14 could be generally possible.

By means of the movement model generation module 16 a movement model m' is generated based on the preprocessed sensor data from the preprocessing module 14.

The real-time analysis module 18 receives and processes data provided by the preprocessing module 14 and the movement model generation module 16.

The real-time analysis module 18 uses the movement model m' created by the movement model generation module 16 in real-time in order to deduce the probability density function of the movement phase.

Then, the data are transferred from the real-time analysis module 18 to the filter 20.

The filter 20 filters the data provided by the real-time analysis module 18.

The filter 20 represents the phase probability density function as a set of particles.

Not shown in FIG. 7 is that for gait, the gait speed of the movement phase is retrieved as a single normal distribution to be used in the filter 20.

By means of the filter 20, estimation of previous time steps is taken into account to get a movement phase, e.g. a gait phase, that is consistent in time.

Thus, the filter 20 allows to establish a best estimate for the true value of the movement model m from an incomplete, potentially noisy set of observations on that movement model m and the corresponding movement.

The movement model m is translated into stimulation data d.

In this embodiment, the control system 10 programs the IPG 22 to deliver stimulation according to the stimulation data d.

In this embodiment, the control system 10 is body worn. However, also non-body worn alternatives are possible.

Not shown in FIG. 7 is that the control system 10 extracts at least one base frequency out of sensor input data.

In particular, the base frequency is indicative of a cadence of the movement.

The cadence of the left foot should be equal to the cadence of the right foot and the cadence of the provided stimulation, and the left foot and right foot should be (roughly) in anti-phase.

Not shown in FIG. 7 is that the control system 10 could also be used for a reconstruction and/or restoration system for cyclic movements other than gait, including but not limited to stepping, swimming, rowing or cycling.

Not shown in FIG. 7 is that the control system 10 may comprise a pre-warning module, which is configured and arranged to provide a pre-warning signal indicative of providing an upcoming stimulation event.

Figure 8:
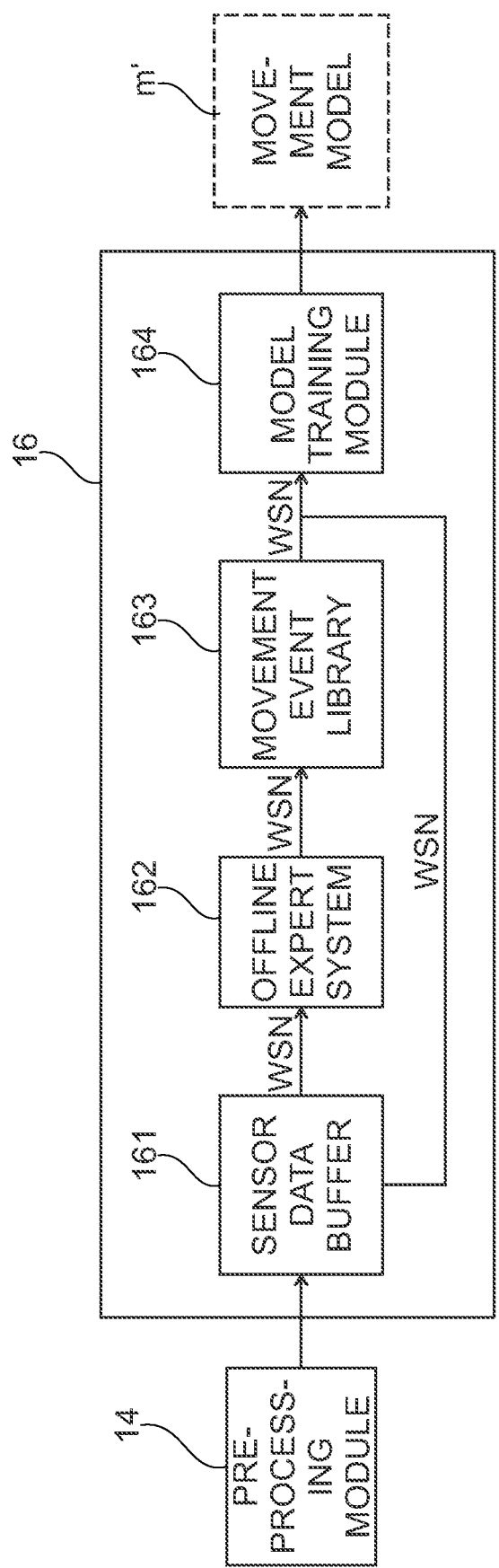
FIG. 8 a schematic drawing of the movement model generation module.

FIG. 8 shows a schematic drawing of the movement model generation module.

The movement model generation module 16 of the control system 10 disclosed in FIG. 7 comprises a sensor data buffer 161.

In other words, the control system 10 may comprise at least one sensor data buffer 161.

The movement model generation module 16 further comprises an offline expert system 162.

The movement model generation module 16 may comprise further offline expert systems 162.

In other words, the control system 10 comprises at least one offline expert system.

The movement model generation module 16 further comprises a movement event library 163.

In another embodiment, the movement model generation module 16 could also comprise more than one movement event library 163.

In other words, the control system 10 could comprise at least one movement event library 163.

In this embodiment, the movement model generation module 16 further comprises a model training module 164.

In another embodiment, the movement model generation module 16 could comprise more than just one model training module 164.

In other words, the control system 10 could comprise at least one model training module 164.

The sensor data buffer 161 is connected to the offline expert system 162.

The offline expert system 162 is connected to the movement event library 163.

The movement event library 163 is connected to the model training module 164.

As disclosed in FIG. 7, the movement model generation module 16 of the control system 10 is connected to the preprocessing module 14 of the control system 10.

The connections between the sensor data buffer 161 and the offline expert system 162, the offline expert system 162 and the movement event library 163, the movement event library 163 and the model training module 164 is a direct connection.

However, also an indirect connection (i.e. with another component of the model training module 16 in between) would be generally possible.

The connections between the sensor data buffer 161 and the offline expert system 162, the offline expert system 162 and the movement event library 163, the movement event library 163 and the model training module 164 is a wireless connection WSN.

However, also a cable-bound connection would be generally possible.

The connection between the movement model training module 16 and the preprocessing module 14, as disclosed in FIG. 7, is in this embodiment a wireless connection WSN.

However, also a cable-bound connection would be generally possible.

Preprocessed sensor data (compare FIG. 7) are transferred from the preprocessing module 14 to the sensor data buffer 161 of the movement model generation module 16.

The sensor data buffer 161 stores preprocessed sensor data.

In this embodiment, data are recorded for a complete rehabilitation session.

However, shorter periods of data recording could be generally possible.

However, data should be recorded for a period of time of minimum one complete movement, e.g. gait cycle.

Based on the accumulated sensor data in the sensor data buffer 161, the offline expert system 162 determines a movement event library 163 comprising a list of different gait events and phase offline.

The offline expert system 162 may allow to use criteria that could not be used in real-time.

It could be possible to use the created gait phase offline at any time.

Possible gait events in the movement event library 163 could include but are not limited to initial ground contact, heel strike, foot flat, loading response, midstance, terminal stance, heel off, preswing, toe off, initial swing, midswing, terminal swing, and/or heel strike.

However, it is possible that there are only two events (foot-strike and foot-off) for gait/walking.

Note that the movement event library 163 determined by the offline system 162 is characterized by showing always the same value at the same event and being a linear interpolation between two consecutive events.

Based on the movement event library 163, the model training module 164 trains the movement model m', here the gait model m', using recent preprocessed sensor data in the sensor data buffer 161 to adapt the movement model m' to the particular movement of the patient.

In other words, the model training module 164 prepares and provides the movement model m' on the basis of a fusion of sensor input data and a previous movement model m'.

In other words, the movement model generation module 16 is a learning system.

In other words, various preprocessed sensor data from the preprocessing module 14 update the sensor data buffer 161 and as soon as a whole gait cycle is detected, the past gait event is determined online by the model training module 164.

It is possible that the sensor data buffer 161 could comprise accumulated preprocessed sensor data from one patient, such as several or multiple recording sessions, and/or from two or more patients and/or from one or more trainers and/or from one or more healthy subjects.

Beyond a movement model m' for gait cycle (i.e. gait model), the movement model generation module 164 could prepare and provide the movement model m' on the basis of a fusion of sensor input data and a previous movement model m' for various movements, including but not limited to stepping, cycling, swimming, running, rowing.

The example control and estimation routines included herein can be used with various system configurations. The control methods and routines disclosed herein may be stored as executable instructions in non-transitory memory and may be carried out by a control system 10 e.g. as a part of the movement model generation module 16 in combination with the input module 12, the preprocessing module 14, the real-time analysis module 18, the filter 20, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the control system 10, where the described actions are carried out by executing the instructions in a control system 10 including the various hardware components.

REFERENCES 10 control system
12 input module
14 preprocessing module
16 movement model generation module
18 (real-time) analysis module
20 filter
22 implantable pulse generator (IPG)
24 sensor
161 sensor data buffer
162 offline expert system
163 (movement) event library
164 model training module
d stimulation data
m movement model
m' movement model
CMB custom muscle blocks
FMB functional muscle block
IPG implantable pulse generator
TEL connection, telemetry line
WSN wireless network
LVLat left vastus lateralis
RVLat right vastus lateralis
LIl left iliopsoas
RIl right iliopsoas
LRF left rectus femoris
RRF right rectus femoris
LST left semitendinosus
RST right semidentinosus
LTA left tibialis anterior
RTA right tibialis anterior
LMG left medial gastrocnemius
RMG right medial gastrocnemius
LSol left soleus
RSol right soleus
LFHL left flexor halluces longus
RFHL right flexor halluces longus

The invention claimed is:

1. A control system for a movement reconstruction and/or restoration system for a patient, comprising:
a movement model generation module to generate movement model data information; and
an analysis module receiving and processing data provided at least by the movement model generation module;
wherein the control system is configured and arranged to prepare and provide on the basis of data received by the movement model generation module and the analysis module a movement model describing a movement of a patient and providing, on the basis of the movement model, stimulation data for movement reconstruction and/or restoration; and wherein the movement model generation module comprises a filter to establish an estimate for a true value of the movement model from a set of observations on the movement model.

2. The control system according to claim 1, wherein the analysis module is a real-time analysis module.

3. The control system according to claim 2, wherein the control system further comprises an input module for receiving sensor input data, the sensor input data describing a phase of the movement.

4. The control system of claim 3, wherein the control system further comprises a preprocessing module for preprocessing sensor input data received by the input module.

5. The control system of claim 3, wherein the filter is at least one of a Kalman filter, a histogram filter, a particle filter, or a stochastic filter.

6. The control system of claim 3, wherein the movement model generation module is configured and arranged to prepare and provide the movement model, wherein the movement model generation module is a learning system.

7. The control system of claim 6, wherein the control system is configured and arranged to prepare and provide the movement model on the basis of a fusion of sensor input data and movement model.

8. The control system of claim 3, wherein the control system comprises at least one sensor data buffer.

9. The control system of claim 3, wherein the control system comprises at least one offline expert system.

10. The control system of claim 3, wherein the control system comprises at least one movement event library.

11. The control system of claim 3, wherein the control system comprises at least one model training module.

12. The control system of claim 3, wherein the control system is configured and arranged to extract at least one base frequency out of sensor input data, wherein the base frequency is indicative of a cadence of the movement.

13. The control system of claim 3, wherein the control system comprises a pre- warning module, which is configured and arranged to provide a pre-warning signal indicative of providing an upcoming stimulation event.

14. The control system of claim 3, wherein the filter is a non-linear digital filter that estimates a joint probability distribution over a set of unknown variables for each of a set of timeframes using a series of measurements observed over time.

15. The control system of claim 14, wherein the filter is a Kalman filter.

* * * * *